United States Patent [19]

Mitchell

[11] Patent Number: 5,095,155

[45] Date of Patent: Mar. 10, 1992

[54] PROCESS FOR THE SEPARATION OF ISOMERS OF DIASTEREOMERIC ALCOHOLS

[75] Inventor: Peter W. D. Mitchell, Freehold, N.J.

[73] Assignee: Union Camp Corporation, Wayne, N.J.

[21] Appl. No.: 534,800

[22] Filed: Jun. 7, 1990

[51] Int. Cl.$^5$ .................. C07C 37/68; C07C 35/00
[52] U.S. Cl. .................. 568/820; 560/349; 560/256; 568/821; 568/822; 568/827; 568/875; 568/877; 568/868
[58] Field of Search ............... 568/820, 821, 822, 875, 568/810, 827, 877, 868; 560/249, 868, 256

[56] References Cited

U.S. PATENT DOCUMENTS

| 3,729,503 | 4/1973 | Gribou et al. | 560/249 |
| 3,860,635 | 1/1973 | Kitchens | 568/820 |

FOREIGN PATENT DOCUMENTS

| 18828 | 2/1977 | Japan | 568/820 |
| 34707 | 3/1978 | Japan | 568/875 |
| 780428 | 4/1982 | U.S.S.R. | 568/820 |

*Primary Examiner*—Werren B. Lone
*Attorney, Agent, or Firm*—William K. Wissing

[57] ABSTRACT

Closely boiling diastereomeric isomer alcohols are separated by converting them to esters having disparate boiling points, separating the ester isomers by distillation and saponifying the separate ester isomers to obtain the individual alcohol isomers.

4 Claims, No Drawings

PROCESS FOR THE SEPARATION OF ISOMERS OF DIASTEREOMERIC ALCOHOLS

BACKGROUND OF THE INVENTION

1. Field of the Invention

The present invention relates to methods of separating diasteromeric isomers, and more particularly to the separation of isomers of diastereomeric alcohols.

2. Brief Description of the Prior Art

Isomers of diastereomeric alcohols are separable by a number of techniques such as by fractional distillation, crystallization, crystallization of derivatives such as hydrogen phthalates or para-nitro benzoates, and chromatography. The particular method of separation to be employed is generally chosen on the basis of cost and separation efficiency.

Distillation is often the preferred separative technique. It is usually an efficient, less costly, and less labor intensive process that is more easily adaptable to large scale production, in comparison with other techniques. However, distillation has not been a viable option for the separation of a number of isomers of diastereomeric alcohols, in particular those isomers where the alcohols have boiling points that are very close to each other. In such instances, resort must be made to crystallization, chromatography or other techniques, with their higher cost and other associated disadvantages. The latter is the case with the isomeric pair alpha-fenchol and beta-fenchol, which have a boiling point difference of only 0.3° C.

Efficient and cost effective separative techniques for such closely boiling alcohol isomers are needed. The present invention is directed to this important end.

SUMMARY OF THE INVENTION

The present invention permits the efficient and economical separation of diastereomeric isomeric alcohols of very close boiling points by a procedure which employs distillative techniques that had heretofore been ineffective in such separations. Specifically, the subject invention is directed to a process for the separation of a mixture of diastereoisomeric alcohols, said process comprising esterifying the mixture of diastereoisomeric alcohols to obtain a mixture of corresponding diastereoisomeric esters, distilling the mixture of diastereoisomeric esters to obtain separate diastereoisomeric esters, and saponifying at least one of the separated diastereoisomeric esters to obtain a separate diastereoisomeric alcohol.

DETAILED DESCRIPTION OF THE INVENTION

The subject invention is based, in part, on the surprising realization that the boiling point difference of esters of diastereomeric isomeric alcohol isomer pairs may be greater than that of its unesterified counter part, and that this boiling point difference increases as the molecular weight of the ester pairs is increased.

The method of the invention is particularly applicable to diastereomeric isomeric alcohols, referred to herein as diastereoisomeric alcohols, having a boiling point difference too small to enable their substantial separation by conventional fractional distillation techniques. The term "substantially inseparable by conventional fractional distillation techniques", as used herein, means diastereoisomeric alcohols having boiling points so close that a product of the distillation will contain a substantial proportion of each isomer. Most preferably, the process is applied to diastereoisomeric alcohols having boiling points within about 1° C. of each other.

The diastereoisomeric alcohols which may be employed in the process of the present invention can be any of the diastereomeric isomers alcohols known, such as the diastereoisomer pairs borneol and isoborneol, alphafenchol and beta-fenchol, menthol and neomenthol, and the like. Preferably, the diastereoisomeric alcohols are those where the isomers have such close boiling points as to make them substantially inseparable by conventional fractional distillation techniques. Such isomers are well known, and include, for example, the diastereoisomer pair alpha-fenchol and beta-fenchol.

As an initial step in carrying out the process of the invention, mixtures of the diastereoisomeric alcohols are esterified with an organic acid to obtain mixtures of the corresponding diastereoisomeric esters. Advantageously, the organic acid employed in the esterification is a monocarboxylic acid, such as a monocarboxylic acid of the formula

$$R-COOH \qquad (I)$$

wherein R represents a hydrocarbyl, or a hydrocarbyl substituted with an inert group.

The term "hydrocarbyl", as used herein, means the monovalent moiety obtained upon removal of a hydrogen atom from a parent hydrocarbon. Illustrative of such hydrocarbyls are alkyl groups, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, and isomeric forms thereof; cycloalkyl groups, such as cyclopropyl, cyclobutyl, cyclopentyl, cyclohexyl, cycloheptyl, cyclooctyl, 2-methylcyclopentyl, 2,3-dimethyl-cyclobutyl, 4-methylcyclobutyl, 3-cyclopentylpropyl, and the like; cycloalkenyl groups, such as cyclobutenyl, cyclopentenyl, cyclohexenyl, cycloheptenyl, cyclooctenyl, and the like, and isomeric forms thereof; cycloalkadienyl groups, such as cyclopentadientyl, cyclohexadienyl, cycloheptadienyl, and the like; aryl groups, such as phenyl, tolyl, xylyl, naphthyl, biphenylyl, and the like; aralkyl groups, such as benzyl, phenethyl, phenpropyl, naphthmethyl, and the like.

The term "hydrocarbyl substituted with an inert group", as used herein, means a hydrocarbyl group as defined above wherein one or more hydrogen atoms have been replaced with a group such as a halogen, nitro, amino, thiocyano, hydroxy, cyano, or alkoxy group.

Preferably R represents a hydrocarbyl which is an alkyl group.

The monocarboxylic acids of formula (I) are well known compounds. Representative of such compounds are the saturated or unsaturated, straight or branched chain aliphatic carboxylic acids, for example, formic acid, acetic acid, propionic acid, butyric acid, isobutyric acid, tert-butylacetic acid, valeric acid, isovaleric acid, caproic acid, caprylic acid, decanoic acid, dodecanoic acid, lauric acid, tridecanoic acid, myristic acid, pentadecanoic acid, palmitic acid, margaric acid, stearic acid, acrylic acid, crotonic acid, undecyenic acid, oleic acid, hexynoic acid, heptynoic acid, octynoic acid, and the like; the saturated or unsaturated, alicyclic carboxylic acids, for example, cyclopentenecarboxylic acid, methylcyclopentenecarboxylic acid, cyclohexanecarboxylic acid, dipropylcyclohexanecarboxylic acid, and the like; the saturated or unsaturated, alicyclic aliphatic carboxylic acids, for example, cyclopentanepropionic acid, cyclohexanebutyric acid, and the like; the aromatic carboxylic acids, for example, benzoic acid, toluic acid, naphthoic acid, ethylbenzoic acid, isobutylbenzoic acid, and the like; and the aromatic aliphatic carboxylic acids, for example, phenylacetic acid, phenylpropionic acid, phenylvaleric acid, cinnamic acid, and the like. Also representative of the carboxylic acids which may be employed in the esterification step of the process of the invention are the above described monocarboxylic acids which are substituted with inert groups, such as, for example, halogen, nitro, amino, thiocyano, hydroxy, cyano, and alkoxy groups. Illustrative of carboxylic acids which are substituted with inert groups are the mono-, di-, and trichloracetic acids; chloropropionic acid; bromobutyric acid; iodovaleric acid; mevalonic acid; 2- and 4-chlorocyclohexanecarboxylic acid; shikimic acid; 2-nitro-1-methylcyclobutanecarboxylic acid; 1,2,3,4,5,6-hexchlorocyclohexanecarboxylic acid; 3-bromo-2-methylcyclohexanecarboxylic acid; 5- and 6-bromo-2-methylcyclohexanecarboxylic acid; 2,3-dibromo-2-methylcyclohexanecarboxylic acid; 2,5-dibromo-2-methylcyclohexanecarboxylic acid; 4,5-dibromo-2-methylcyclohexanecarboxylic acid; 5,6-dibromo-2-methylcyclohexanecarboxylic acid; 3-dibromo-3-methylcyclohexanecarboxylic acid; 6-dibromo-3-methylcyclohexanecarboxylic acid; 2-dibromo-4-methylcyclohexanecarboxylic acid; 1,2-dibromo-4-methylcyclohexanecarboxylic acid; 3-dibromo-2,23-trimethylcyclopentranecarboxylic acid; 1-bromo-3,5-dimethylcyclohexanecarboxylic acid; homogentisic acid; o-, m-, and p-chlorobenzoic acid; anisic acid; salicylic acid; p-hydroxybenzoic acid; B-resorcyclic acid; gallic acid; veratric acid; trimethyxybenxoic acid, trimethoxycinnamic acid; 4,4'-dichlorobenzylic acid; o-, m-, and p-nitrobenzoic acid; cyanoacetic acid; 3,4- and 3,5-dinitrobenzoic acid; 2,4,6-trinitrobenzoic acid; thiocyanoacetic acid; cyanopropionic acid; lactic acid; ethoxyformic acid (ethyl hydrogen carbonate); butyloxyformic acid; penyloxyformic acid; hexyloxyformic acid; dodecyloxyformic acid; hexadecyloxyformic acid; and the like.

Where available, the anhydrides or other acyl derivatives of the organic acid may also be employed in the esterification step of the subject process.

In selecting a particular organic acid or anhydride thereof for the esterification step, one can also control to some extent the degree of boiling point separation to be obtained for the distillation step to follow. Specifically, it has been discovered that as the molecular weight of the esterifying agent (and therefore the molecular weight of the ester) is increased, the difference in the boiling points of the diastereomeric ester isomers also increases. This serves to facilitate the separation of the esters in the distillation step of the present process. The molecular weight of the esterifying agent, however, should not be so great as to provide a boiling point so high that it will cause ester decomposition during distillation.

In carrying out the esterification step of the process of the invention, a carboxylic acid of formula (I) as described above is added to the diastereoisomeric alcohol mixture. The acid may be provided in a mixture with an inert organic solvent to assist in promoting the esterification. By the term "inert organic solvent", it is meant a solvent which does not enter into or otherwise adversely affect the desired course of the esterification reaction. Suitable solvents will be apparent to those skilled in the art. Representative of such inert organic solvents are hydrocarbon solvents such as benzene, toluene, naphtha, n-hexane, and the like. The diastereoisomeric alcohol mixture may also be dissolved in an inert solvent as defined above, if desired, to facilitate promotion of the desired esterification.

The proportions of the diastereoisomeric alcohols and carboxylic acids should be such that there is obtained a reaction mixture wherein substantially complete esterification of the alcohols will occur. The rate of the esterification reaction may also be influenced by the stoichiometry employed in the reaction. In general, the presence of a molar excess of the carboxylic acids over the alcohols, will facilitate reaction rate. Preferably, 1 to 5 moles of acid per mole of alcohol is employed, most preferably 1 to 3. Lower proportions of acid may be used, but this will generally result in a lower yield of the desired esters.

Esterification of the alcohols may be promoted, if desired, by carrying out the esterification reaction in the presence of a catalytic proportion of an esterification catalyst. Such catalysts and their uses are well known to those skilled in the art. Representative of such catalysts are the known acid catalysts.

Acid catalysts which may be employed include inorganic acids such as sulfuric acid, hydrochloric acid and nitric acid, as well as mixtures thereof. Organic acids such as para-toluene sulfonic acid may also be used. Moreover, ion exchange resins in the acid form may also be employed. In general, any type of acid catalyst known in the art to catalyze esterification reactions may be employed. When an anhydride is used as the esterifying agent, pyridine is most preferred as an esterification catalyst.

A catalytic proportion of the esterification catalyst is generally within the range of from about 0.001 percent to about 20 percent by weight of the diastereoisomeric alcohol present in the reaction mixture, preferably from about 0.1 to about 10 percent by weight, and most preferably 0.5 to 5 percent.

In carrying out the esterification reaction, the alcohol, carboxylic acid (I), and catalyst may be added together in any desired order. The esterification may be carried out at temperatures ranging from room temperature to temperatures just below the boiling point of the diastereoisomeric alcohol. Most of the esterification reactions within the scope of the process of the invention may be advantageously carried out at temperatures within the range of from about 60° C. to 160° C., more preferably within the range of from about 80° C. to about 150° C., and most preferably about 100° C. The esterification may be carried out at sub-atmospheric or super-atmospheric pressures, if desired. However, there is generally no great advantage to carrying out the process of the invention under other than ambient reaction vessel pressures occurring at the temperature under which the esterification reaction is conducted. The esterification is generally completed within a period of from about 3 to about 50 hours, with optimum periods being about 12 hours.

As will be appreciated by those skilled in the art, the rate of reaction is influenced by a number of factors such as the temperature and pressure selected for carrying out the esterification step. Higher temperatures will increase the rate of reaction but may also promote undesirable decompositions of the ester product. Higher temperatures may be tolerated when short reaction times are available. To promote the rate of reaction, the reaction mixture may be agitated, if desired.

The resultant diastereoisomeric ester mixtures can be analyzed by gas chromatography (GC) using literature techniques such as the techniques described in Abbot, *J. Chromalog. Science*, Vol. 21, pp. 425-428 (1983), and Sauna-Calisto et al., *J. Chromalog. Science*, Vol. 21, pp. 267-271 (1983) to determine the boiling point differences of the isomers contained therein. These methods are capable of analyzing both isomers together on non-polar columns, and the boiling point differences are easily estimated from the retention time differences between the two peaks on the chromatogram.

The diastereoisomeric esters in the mixture resulting from the esterification step of the subject process may then be separated, one from the other, immediately upon completion of the desired esterification, which is generally when esterification is 97-98 % complete. Alternatively, the crude reaction mixture may be stored for a period of time before further processing.

At some point, however, in accordance with the process of the invention, the diastereomeric isomeric esters are separated. Such separation is carried out using conventional distillative techniques. Distillation is a well known technique for the separation of compounds having disparate boiling points and, accordingly, a detailed description of the distillation is not needed herein.

The distillation separated diastereoisomeric esters may then be saponified, resulting in separate diastereoisomeric alcohols. In the saponification step of the process of the invention, the esters are treated with aqueous caustic at temperatures up to reflux temperatures, thereby converting the alcohol esters to the desired alcohol products.

Specifically, the saponification step is carried out by reacting the esters with an aqueous alkaline solution of about 25% to about 45% alkaline. The solution may be a solution of caustic alkali such as sodium hydroxide, calcium hydroxide, lithium hydroxide, and the like. Preferably the solution is a solution of about 25% to about 45%, most preferably about 40%, by weight of sodium hydroxide. Caustic alkali solutions of higher alkali concentration are generally not practical and may cause problems as a result of the precipitation of excess caustic as the carboxylate, while lower concentration may reduce the desired rate of saponification and will require reactor vessels of larger capacity.

The saponification step may be carried out at temperatures within the range of room temperature (about 25° C.) to the reflux temperature of the reaction mixture. Preferably, the saponification step is carried out at a temperature of from about 100° C. to about 125° C.

The saponification step may be carried out at atmospheric or super-atmospheric pressure. Generally the autogenous pressure developed by carrying out the reaction in a closed vessel provides satisfactory results. The saponification may also be promoted, if desired, by the addition of any known promoting catalyst, in a catalytic proportion.

The progress of the reaction leading to saponification completion may be monitored by conventional analytical techniques and halted at any desired point. For example, the saponification mixture may be sampled periodically, and an aliquot subjected to gas-liquid chromatography to observe the disappearance of the starting esters. In general, saponification is complete within about 1 to about 12 hours for a given volume of reaction mixture.

The product alcohols delivered from the saponification step are in admixture with substantial proportions of caustic. If desired, the mixture may be washed with a sufficient proportion of a carboxylic acid such as acetic acid, to neutralize the excess caustic. The neutralized alcohol mixture may then be washed with water and subjected to further distillations to improve the product purity.

The following provide Examples of the manner and process of making and using the invention. These Examples should not be construed as limiting the scope of the invention, as set forth in the appended Claims. In the Examples which follow, all parts are by weight and all temperatures are in degrees Celsius, unless otherwise indicated.

EXAMPLE 1

Mixtures of the isomeric pairs borneol and isoborneol, alpha-fenchol and beta-fenchol, and neomenthol and menthol (0.5 g each) were heated at 100° C. for two hours with an equal weight of the anhydrides of acetic acid, propionic acid and butyric acid in the presence of pyridine as catalyst. The solutions were then diluted with water, and the precipitated oils extracted into methylene chloride. The extract was washed with water until free from carboxylic acid anhydride and pyridine, then dried over anhydrous $K_2CO_3$, and analyzed using GC to determine boiling point differences of the ester isomers present in the extract.

The results of the analysis are shown in Table 1. The results reveal that the difference between the boiling points of the ester isomers increase as the molecular weight of the esters increases.

TABLE 1

| Alcohol Isomers | Boiling Point Differences of Esters* | | |
|---|---|---|---|
| | Acetates | Propionates | Butyrates |
| Borneol Isoborneol | 0 | 1.1 | 1.6 |
| α-Fenchol β-Fenchol | 1 | 2 | 3 |
| Neomenthol Menthol | 2.6 | 5.4 | 11.4 |

*In each case, the first listed isomer in each alcohol pair was the lower boiling isomer.

EXAMPLE 2

A fenchol mixture containing 78% beta-fenchol and 18% alpha-fenchol was acylated with varying amounts of acetic anhydride at varying temperatures. Samples were taken at various intervals and tested to determine the percentage of alpha- and beta-acetate ester formed.

The results are shown in Table 2. As the results reveal, beta-fenchol esterifies faster than alpha-fenchol.

TABLE 2

| Acetylation of Mixed Fenchols | | | | | |
|---|---|---|---|---|---|
| Mole Ratio of Acetic Anhydride | 1.2 | 1.2 | 0.64 | 0.64 | 0.64 |
| Temp. (°C.) | 100 | 100 | 100 | 100 | 22 |
| Time (Hrs) | 1 | 3 | 1.3 | 3 | 17 |
| % Conversion | 85.8 | 92.2 | 53.0 | 53.1 | 58.8 |
| % β-Acetate | 85.6 | 83.2 | 90.3 | 90.2 | 93.6 |

EXAMPLE 3

Esterification of mixed fenchols were carried out substantially as set forth in Example 2, except that anhydrides of propionic and butyric acid were employed.

The results are shown in Table 3. The results reveal a more pronounced trend towards beta-fenchol esterification than alpha-fenchol esterification when lower temperatures and longer reaction times are employed.

TABLE 3

| Preparation of Propionates and Butyrates of Mixed Fenchols | | | | |
|---|---|---|---|---|
| | Proprionates | | Butyrates | |
| Mole Ratio of Anhydride | 0.58 | 0.58 | 0.58 | 0.58 |
| Temp. (°C.) | 100 | 22 | 100 | 22 |
| Time (Hrs) | 2 | 17 | 2 | 17 |
| % Conversion | 44.8 | 51.0 | 49.2 | 52.1 |
| % β-Ester | 87.9 | 92.3 | 86.6 | 92.3 |

EXAMPLE 4

Mixed fenchols were prepared by hydrogenation of L-fenchone in isopropanol using Raney-nickel as a catalyst. The crude product after filtration and evaporation of solvent contained, as a percentage by weight, the following: fenchone (1.4 wt.%), β-fenchol (38.6 wt.%), and α-fenchol (47.9 wt.%), with the remainder consisting of residual solvent. The crude product (124.7 g) then was esterified using butyric anhydride (97.2 g) and pyridine (81 g) at 22° C.

The results are shown in Table 4. As the results reveal, the partial esterification raised the percentage of the beta-isomer from 44.6 in the alcohols to 68 in the esters.

TABLE 4

| Preparation of Fenchol Butyrates | | | |
|---|---|---|---|
| Time (Hrs) | 0.7 | 1.7 | 18 |
| α- and β-Fenchol | 86.6 | 75.2 | 41.1 |
| α-Fenchyl Butyrate | 2.8 | 6.0 | 18.4 |
| β-Fenchyl Butyrate | 9.1 | 1.7 | 39.1 |
| % Fenchol Conversion | 12.1 | 23.7 | 58.3 |
| % β-Fenchyl Butyrate in Mixed α- and β-Butyrates | 76.5 | 74.2 | 68 |

The mixture of alcohols and butyrates (155 g) was then distilled through a packed column of about 15 theoretical plates, at 2.0 mm pressure and at a 1:1 reflux ratio. The lower-boiling alcohol mixture was easily separated from the esters, with no separation of the alcohols occurring, and the ester distillation was continued at 2.0 mm pressure and at 10:1 reflux ratio, until the alpha-ester concentration in the cuts had decreased to 50%. At this point the residual esters (68.4 g) were analyzed and found to contain 83% betafenchyl butyrate. This confirmed that the esters were more separable than the alcohols, as predicted by the boiling differences of 3° C. shown by the GC method.

The residual esters (37.2 g) were then saponified by refluxing for 1.5 hours with KOH (62 g) in ethanol (180 ml) to yield mixed fenchols (25.4 g). The mixed fenchols were re-esterified at 22° C. for 16 hours with butyric anhydride (13.9 g) and pyridine (18.7 g). The mixture of alcohols and esters was distilled with minimal fractionation, to remove the alcohols and alpha-fenchyl butyrate, leaving behind 9.8 g of beta-fenchyl butyrate of 95% purity. This was saponified using KOH (5.9 g) in ethanol (50 g) and the resulting beta-fenchol was flash-distilled to give 5.2 g of beta-fenchol of 95% purity and having an $[\alpha]_D^{23}$ of +26.02.

What is claimed is:

1. A process for the separation of a mixture of diastereoisomeric alcohols which comprises:

esterifying the mixture of diastereoisomeric alcohols with an organic, monocarboxylic acid of the formula R-COOH, wherein R represents a hydrocarbyl, or a hydrocarbyl substituted with an inert group to obtain a mixture of corresponding diastereoisomeric esters;

distilling the mixture of diastereoisomeric esters to obtain separate diastereoisomeric esters; and saponifying at least one of the separated diastereoisomeric esters with an aqueous, caustic solution to obtain a separate diastereoisomeric alcohol.

2. The method of claim 1 wherein the mixture of diastereoisomeric alcohols is a mixture of alcohols which are substantially inseparable by conventional fractional distillation techniques.

3. The method of claim 2 wherein the substantially inseparable alcohols have boiling points within about 1° C. of each other.

4. The method of claim 3 wherein the mixture of diastereoisomeric alcohols is a mixture of alpha-fenchol and beta-fenchol.

* * * * *